United States Patent [19]

Sauer et al.

[11] Patent Number: 4,731,367

[45] Date of Patent: Mar. 15, 1988

[54] 2-SUBSTITUTED ERGOLINES USEFUL AS NEUROLEPTICS AND ANTIDEPRESSANTS

[75] Inventors: Gerhard Sauer; Andreas Huth; Helmut Wachtel; Herbert H. Schneider, all of Berlin, Fed. Rep. of Germany

[73] Assignee: Schering Aktiengesellschaft, Berlin and Bergkamen, Fed. Rep. of Germany

[21] Appl. No.: 721,522

[22] Filed: Apr. 9, 1985

[30] Foreign Application Priority Data

| Apr. 9, 1984 [DE] | Fed. Rep. of Germany | 3413657 |
| Apr. 9, 1984 [DE] | Fed. Rep. of Germany | 3413658 |
| Apr. 9, 1984 [DE] | Fed. Rep. of Germany | 3413659 |
| Apr. 9, 1984 [DE] | Fed. Rep. of Germany | 3413660 |

[51] Int. Cl.$^4$ .................. A61K 31/48; C07F 7/02; C07D 457/04
[52] U.S. Cl. .................. 514/288; 546/14; 546/67; 546/68; 546/69
[58] Field of Search .................. 546/67, 68, 69, 14; 514/288

[56] References Cited

U.S. PATENT DOCUMENTS

| 3,029,243 | 4/1962 | Olin | 546/67 |
| 3,251,846 | 5/1966 | Semonsky et al. | 546/68 |
| 3,953,454 | 4/1976 | Zikan et al. | 546/68 |
| 4,382,940 | 5/1983 | Bernardi et al. | 546/67 |
| 4,500,712 | 2/1985 | Bernardi et al. | 566/68 |

OTHER PUBLICATIONS

Berde, et al., *Ergot Alkaloids and Related Compounds,* Springer-Verlag, New York (1978), pp. 74, 469–470.
Pratt, et al., "Organosilicon Compounds, XX...", *J. Org. Chem.,* vol. 40, (1975), pp. 1090–1093.

*Primary Examiner*—Donald G. Daus
*Assistant Examiner*—Cecilia Shen
*Attorney, Agent, or Firm*—Millen & White

[57] ABSTRACT

Novel ergoline derivatives, substituted in the 2-position, of the formula wherein
$C_8=C_9$ and $C_9=C_{10}$ each independently is a CC-single or a C=C-double bond, but not together a cumulated double bond, and the substituent in the 8-position is in the α- or β-configuration where $C_8=C_9$ is a CC-single bond,
$R^2$ is
CN, SR, SOR, $$-CH\underset{S}{\overset{S}{<}}(CH_2)_n$$

wherein n is 2 or 3, $$-CR\underset{O}{\overset{\|}{}}$$

and —CH(OH)R, wherein R has the meaning of H or $C_{1-4}$-alkyl,
the grouping COR' and CSR' wherein R'=OH, $OC_{1-4}$-alkyl, benzyl, $NH_2$ or NHR",
the grouping CH=CH—$CO_2R$" and $CH_2$—$CH_2$—$CO_2R$" wherein R"=$C_{1-4}$-alkyl,
the grouping C|C—R'" and HC=CH—R'" wherein R'"= hydrogen, $C_{1-4}$-alkyl, phenyl, $CH_2OH$, $CR"_2OH$, $CO_2R$"', $CH_2NR"_2$ or $SiMe_2R"$; $C_{1-3}$-alkyl, or $C_{1-3}$-alkyl substituted by OH or phenyl; or $$\begin{array}{c} Me \\ | \\ Si-R" \\ | \\ Me \end{array}$$

wherein R" is $C_{1-4}$ alkyl,
$R^6$ is $C_{1-4}$-alkyl and
$R^8$ is methyl, NH—CO—$NEt_2$ or NH—CS—$NEt_2$,
and the physiologically acceptable acid addition salt thereof, possess biological efficacy in the region of the central nervous system, e.g., as neuroleptics and antidepressants.

14 Claims, No Drawings

2-SUBSTITUTED ERGOLINES USEFUL AS NEUROLEPTICS AND ANTIDEPRESSANTS

The present invention relates to novel ergoline derivatives of Formula I which are substituted in the 2-position, their preparation according to methods known per se, and their use as medicinal agents based on these compounds.

SUMMARY OF THE INVENTION

It is an object of this invention to provide new substituted ergolinyl compounds having valuable pharmacological properties and are intermediates for the preparation of the same and of each other.

Upon further study of the specification and appended claims, further objects and advantages of this invention will become apparent to those skilled in the art.

These objects have been attained by providing new, substituted ergolines of Formula I

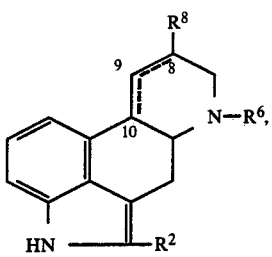

wherein
$C_8 \text{---} C_9$ and $C_9 \text{---} C_{10}$ each independently is a CC-single or a C=C-double bond, but not together a cumulated double bond, and the substituent in the 8-position is in the α- or β-configuration where $C_8 \text{---} C_9$ is a CC-single bond,
$R^2$ is
CN, SR, SOR,

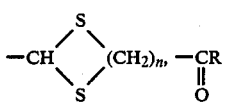

or —CH(OH)R wherein R is H or $C_{1-4}$-alkyl and n is 2 or 3;
the grouping COR' or CSR', wherein R'=OH, OC$_{1-4}$-alkyl, benzyl, NH$_2$ or NHR'';
the grouping CH=CH—CO$_2$R'' or CH$_2$—CH$_2$—CO$_2$R'' wherein R''=$C_{1-4}$-alkyl throughout the above;
the grouping C≡C—R''' and HC=CH—R''' wherein R'''=hydrogen, $C_{1-4}$-alkyl, phenyl, CH$_2$OH, CR''$_2$OH,

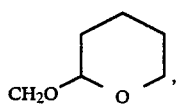

CO$_2$R'', CH$_2$NR''$_2$ or SiMe$_2$R''; $C_{1-3}$-alkyl, or $C_{1-3}$-alkyl substituted by OH or phenyl, or

wherein R'' is $C_{1-4}$-alkyl;
$R^6$ is $C_{1-4}$-alkyl and
$R^8$ is methyl or the grouping NH—CO—NEt$_2$ or NH—CS—NEt$_2$,
and physiologically acceptable salts thereof.

DETAILED DISCUSSION

The salts of the compounds of Formula I according to this invention include acid addition salts and are derived from physiologically acceptable acids. Such physiologically acceptable acids are inorganic acids, e.g., hydrochloric acid, nitric acid, phosphoric acid, sulfuric acid, hydrobromic acid, hydriodic acid, nitrous acid or phosphorous acid, or organic acids, such as, for example, aliphatic mono- or di-carboxylic acids, phenyl-substituted alkanecarboxylic acids, hydroxyalkanecarboxylic acids, or alkanedicarboxylic acids, aromatic acids or aliphatic or aromatic sulfonic acids. Examples for physiologically acceptable salts of these acids include, therefore, the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, -hydroxy-butyrate, glycollate, malate, tartrate, methanesulfonate, propanesulfonate, naphthalene-1-sulfonate or naphthalene-2-sulfonate.

Alkyl residues of up to 3 or 4 carbon atoms throughout the foregoing include those derived from aliphatic hydrocarbons, for example, methyl, ethyl, n-propyl, isopropyl and n-butyl, isobutyl, test-butyl, etc.

As compared with conventional ergolines unsubstituted in the 2-position, for example, lisuride or terguride, the compounds of Formula I according to this invention are distinguished by a centrally dopaminergic and/or α$_2$-receptor-blocking activity.

The central α$_2$-receptor blockage, for example, of 1,1-diethyl-3-(6-methyl-2-methylthio-8α-ergolinyl)urea (A) and of 1,1-diethyl(6-methyl-2-ethynyl-8α-ergolinyl)urea (B) was illustrated in an interaction test with the α$_2$-receptor agonist clonidine on mice after a one-time i.p. pretreatment (parameter" elimination of hypothermia caused by clonidine 0.1 mg/kg i.p.). Male NMRI mice were pretreated with various doses of A and B, respectively, which themselves do not affect the thermoregulation of the test animals, and with a carrier medium, respectively. After 30 minutes all animals received clonidine 0.1 mg/kg i.p. Rectal temperature was measured with the aid of a thermal probe 60 minutes after administration of A or B, or of carrier medium (=30 minutes after clonidine). The mice pretreated with carrier medium exhibited hypothermia. The effect of clonidine, that of lowering body temperature, was significantly reduced or eliminated in correllation with the dose of animals pretreated with compound A or B according to this invention. The clonidine-antagonistic effects of A and of B were statistically significant in a dose as low as 0.2 mg/kg. See Table 1.

Central dopamine receptor blockage of A and B was demonstrated in an interaction test with the dopamine receptor agonist apomorphine in mice after a one-time pretreatment i.p. The test involved elimination of hypothermia caused by apomorphine 5 ng/kg i.p. Male NMRI mice were pretreated with various doses of A and B which themselves do not affect thermoregulation of the test animals, and, respectively, with a carrier medium. Thirty minutes later, all animals received apomorphine 5 mg/kg i.p. Rectal temperature was measured with the aid of a thermal probe 60 minutes after administration of A or B, or of carrier medium (=30 minutes after apomorphine). While the mice pretreated with carrier medium showed hypothermia, the effect of apomorphine of lowering body temperature was significantly reduced in correlation with the dose in animals pretreated with A or B. The apomorphine-antagonistic effects of A and of B were statistically significant in a dose as low as 0.2 mg/kg. See Table 2.

Based on these findings, the compounds of this invention can thus be utilized as neuroleptics for the treatment of psychoses of the schizophrenic array of symptoms or as antidepressants.

In order to use the compounds of this invention as medicinal agents, they are made into pharmaceutical preparations containing, in addition to the active ingredient, pharmaceutical, organic or inorganic, inert excipients suitable for enteral or parenteral administration. These include, for example, water, gelatin, gum arabic, lactose, amylose, magnesium stearate, talc, vegetable oils, polyalkylene glycols, etc. The pharmaceutical preparations can be present in the solid form, e.g., as tablets, dragees, suppositories, capsules, or in the liquid for, for example as solutions, suspensions or emulsions. If desired, they may contain auxiliary agents, such as preservatives, stabilizers, wetting agents or emulsifiers, salts for varying the osmotic pressure, or buffers.

The pharmacologically active compounds of this invention can be processed in accordance with conventional methods of galenic pharmacy to produce for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oil or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.5-5 mg. In a pharmaceutically acceptable carrier per unit dosage.

The dosage of the compounds according to this invention generally is 0.5-20 mg/kg/day when administered to patients, e.g., humans as a neuroleptic analogously to the known agent haloperidol, and is 0.5-20 mg/kg/day when administered as an antidepressant analogously to the known agent mianserin.

Dosages for a given host can be determined using conventional considerations, e.g., by customary comparison of the differential activities of the subject compound and of a known agent, e.g., by means of an appropriate, conventional pharmacological protocol.

TABLE 1

Antagonistic effect of pretreatment (30 min. i.p.) with various doses of 2-substituted ergoline ureas on hypothermia in mice triggered by clonidine (0.1 mg/kg i.p.). Rectal temperature of test animals was measured 30 min. after clonidine (=60 min. after test compound)
(*: $p < 0.05$, **: $p <$ vs. control; variance analysis/Dunnett test).

| Compound | n | Control | 0.05 | 0.1 | 0.2 | 0.39 |
|---|---|---|---|---|---|---|
| | | Rectal Temperature [°C.] (Average Values ± S.E.M.) Dose of Test Compound [mg/kg] | | | | |
| TDHL | 8 | 33.1 ± 0.2 | — | — | — | 33.6 ± 0.2 |
| 2-C≡CH—TDHL | 8 | 34.6 ± 0.2 | 33.9 ± 0.2 | 34.5 ± 0.2 | 35.3 ± 0.2 | 35.6 ± 0.3* |
| 2-SCH$_3$—TDHL | 8 | 33.6 ± 0.1 | 34.2 ± 0.1 | 34.2 ± 0.2 | 35.4 ± 0.3** | 35.3 ± 0.1** |
| 2-CH$_3$—TDHL | 8 | 34.1 ± 0.2 | — | — | 34.3 ± 0.3 | 34.8 ± 0.2 |
| 2-SC$_2$H$_5$—TDHL | 8 | 33.7 ± 0.2 | — | 34.4 ± 0.2 | 34.0 ± 0.3 | 34.9 ± 0.4* |
| 2-SCH(CH$_3$)$_2$—TDHL | 8 | 34.0 ± 0.2 | — | 34.0 ± 0.2 | 34.8 ± 0.2 | 34.6 ± 0.2 |
| 2-SC$_3$H$_2$—TDHL | 8 | 33.7 ± 0.1 | — | — | 34.1 ± 0.2 | 34.4 ± 0.2* |

| Compound | n | 0.78 | 1.56 | 3.13 | 6.26 | 12.5 |
|---|---|---|---|---|---|---|
| | | Rectal Temperature [°C.] (Average Values ± S.E.M.) Dose of Test Compound [mg/kg] | | | | |
| TDHL | 8 | 33.7 ± 0.3 | 34.1 ± 0.3** | 34.7 ± 0.2** | 34.8 ± 0.3** | — |
| 2-C≡CH—TDHL | 8 | 35.7 ± 0.3** | 35.9 ± 0.2** | — | — | — |
| 2-SCH$_3$—TDHL | 8 | 35.4 ± 0.2** | 35.4 ± 0.3** | 35.9 ± 0.3** | — | — |
| 2-CH$_3$—TDHL | 8 | 35.2 ± 0.2** | 36.0 ± 0.2** | 35.9 ± 0.2** | — | — |

TABLE 1-continued

Antagonistic effect of pretreatment (30 min. i.p.) with various doses of 2-substituted ergoline ureas on hypothermia in mice triggered by clonidine (0.1 mg/kg i.p.). Rectal temperature of test animals was measured 30 min. after clonidine (=60 min. after test compound)
(*: $p < 0.05$, **: $p <$ vs. control; variance analysis/Dunnett test).

| | | | | | | |
|---|---|---|---|---|---|---|
| 2-SC$_2$H$_5$—TDHL | 8 | 35.5 ± 0.6** | 34.7 ± 0.5 | 35.9 ± 0.2** | — | — |
| 2-SCH(CH$_3$)$_2$—TDHL | 8 | 35.3 ± 0.2** | 36.2 ± 0.3** | 37.0 ± 0.3** | — | — |
| 2-SC$_3$H$_2$—TDHL | 8 | 34.6 ± 0.2** | 34.7 ± 0.2** | 35.8 ± 0.1** | — | — |

TDHL = 1.1-Diethyl-(6-methyl-8α-ergolinyl)urea

TABLE 2

Antagonistic effect of pretreatment (30 min. i.p.) with various doses of 2-substituted ergoline ureas on hypothermia in mice triggered by apomorphine (5 mg/kg i.p.). Rectal temperature of test animals was measured 30 min. after apomorphine (=60 min. after test compound)
(*: $p <0.05$, **: $p <0.01$ vs. control; variance analysis/Dunnett test).

| | | Rectal Temperature [°C.] (Average Values ± S.E.M.) Dose of Test Compound [mg/kg] | | | | |
|---|---|---|---|---|---|---|
| Compound | n | Control | 0.05 | 0.1 | 0.2 | 0.39 |
| TDHL | 8 | 32.5 ± 0.4** | — | — | — | — |
| 2-C≡CH—TDHL | 8 | 34.0 ± 0.3 | 33.6 ± 0.5 | 33.7 ± 0.5 | 36.1 ± 0.4** | 36.6 ± 0.4** |
| 2-SCH$_3$—TDHL | 8 | 32.9 ± 9.4 | 34.3 ± 0.5* | 33.9 ± 0.3 | 34.7 ± 0.4** | 35.8 ± 0.3** |
| 2-CH$_3$—TDHL | 8 | 33.7 ± 0.5 | — | — | 33.0 ± 0.4 | 33.2 ± 0.3 |
| 2-SC$_2$H$_5$—TDHL | 8 | 32.7 ± 0.3 | — | 33.3 ± 0.2 | 33.7 ± 0.4 | 34.1 ± 0.7 |
| 2-SCH(CH$_3$)$_2$—TDHL | 8 | 33.1 ± 0.3 | — | — | 33.0 ± 0.3 | 33.0 ± 0.3 |
| 2-SC$_3$H$_7$—TDHL | 8 | 33.0 ± 0.6 | — | 32.9 ± 0.3 | 33.1 ± 0.3 | 33.5 ± 0.6 |

| | | Rectal Temperature [°C.] (Average Values ± S.E.M.) Dose of Test Compound [mg/kg] | | | | |
|---|---|---|---|---|---|---|
| Compound | n | 0.78 | 1.56 | 3.13 | 6.25 | 12.5 |
| TDHL | 8 | 33.9 ± 0.5 | 33.8 ± 0.4 | 35.1 ± 0.5** | 35.5 ± 0.5** | 36.0 ± 0. |
| 2-C≡CH—TDHL | 8 | 37.3 ± 0.2** | 36.7 ± 0.2** | 35.7 ± 0.3** | — | — |
| 2-SCH$_3$—TDHL | 8 | 35.5 ± 0.2** | 35.5 ± 0.3** | — | — | — |
| 2-CH$_3$—TDHL | 8 | 34.3 ± 0.3 | 34.1 ± 0.3 | 35.0 ± 0.2** | 35.5 ± 0.2** | — |
| 2-SC$_2$H$_5$—TDHL | 8 | 35.2 ± 0.5** | 34.8 ± 0.4** | 35.5 ± 0.4** | — | — |
| 2-SCH(CH$_3$)$_2$—TDHL | 8 | 33.4 ± 0.5 | 34.3 ± 0.4 | 34.0 ± 0.4 | 34.2 ± 0.5 | — |
| 2-SC$_3$H$_7$—TDHL | 8 | 33.9 ± 0.5 | 33.9 ± 0.5 | 34.7 ± 0.6 | — | — |

TDHL = 1.1-Diethyl-(6-methyl-8α-ergolinyl)urea

The compounds of this invention of Formula I wherein R$^2$ is CN, SR, SOR,

and —C(HOH)R where R is C$_{1-4}$-alkyl, can be prepared from compounds of Formula II

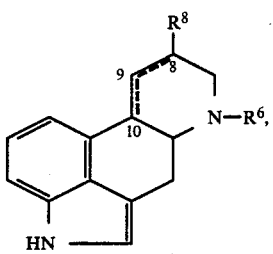

according to conventional methods wherein C$_8$---C$_9$, C$_9$---C$_{10}$, R$^6$ and R$^8$ have the meanings indicated in Formula I above, e.g., by reaction with an appropriate electrophilic reagent.

When the substituent R$^2$ represents the nitrile group, then the process is performed by adding chlorosulfonyl isocyanate to the ergoline of Formula II in an inert solvent, such as acetonitrile or dimethylformamide, in the presence of a base, such as trimethyl- or triethylamine (cf. DOS 2,365,974). The use of an inert gas atmosphere is advantageous. The reaction is completed after 10-50 hours at room temperature.

Where the substituent R$^2$ represents the S-alkyl or S-methyl group, then the process is conducted by adding the sulfonium salt, for example, the dimethylmethylthiosulfonium fluoborate, to the ergoline of Formula II in an inert solvent such as dioxane or tetrahydrofuran. The reaction is terminated after 0.5-2 hours at room temperature.

Where the substituent R$^2$ signifies an acyl group, then the process is performed by reacting the ergoline of Formula II with the acyl chloride in the presence of a Lewis acid, e.g., aluminum trichloride. However, if the acyl chloride is not in liquid form, then nitrobenzene or chlorobenzene can be utilized as the solvent. The reaction is preferably conducted at temperatures below room temperature, such as −10° to −5° C., and is finished after 1-5 hours.

Any carbonyl groups that may be present in substituent R$^2$ can be reduced to hydroxy groups with a complex metal hydride. Such metal hydrides may be sodium borohydride in a protonic or aprotic solvent, e.g., tetrahydrofuran, acetonitrile, dioxane, dimethoxyethane, methanol, ethanol or isopropanol. Anhydrous calcium chloride may be added, preferably at the boiling temperature of the solvent employed or of the reaction mixture.

The oxidation of the methylthio group to the sulfoxide takes place with an aqueous solution of sodium periodate in acetonitrile. After several hours, the reaction is terminated at 50° C.

The compounds of this invention according to Formula I wherein $R^2$ is $C_{1-3}$-alkyl which can be substituted with OH or phenyl; $C_{2-3}$-alkenyl; CONHR'; CSNHR'; COOR', wherein R' means H or $C_{1-3}$-alkyl; or

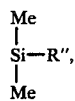

wherein R" means lower alkyl of up to 4 carbon atoms, can be prepared from compounds of Formula III

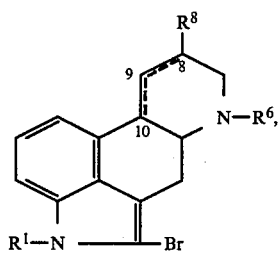

wherein
$C_8 \text{---} C_9$, $C_9 \text{---} C_{10}$, $R^6$ and $R^8$ having the meanings given above and
$R^1$ stands for
Si(R')$_2$R (R'=methyl or phenyl and R=$C_{1-4}$-alkyl), for $C_{1-7}$-alkyl or $C_{7-9}$-aralkyl or for $C_{2-5}$-acyl or arylsulfonyl.

In the first stage of preparation, a 2-bromoergoline derivative of Formula III is reacted with an alkyllithium or with phenyllithium at low temperatures in an inert solvent to form the corresponding 2-lithium ergoline derivative of Formula IV

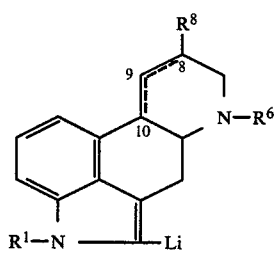

$C_8 \text{---} C_9$, $C_9 \text{---} C_{10}$, $R^1$, $R^6$ and $R^8$ have the meanings given above. Especially suitable as the alkyllithium is tert-butyllithium. The desired compounds may then be prepared from Formula IV by conventional methods.

The substituent $R^1$ occurring in the starting compounds of Formula III in the 1-position has the function of a blocking group. The blocking group $R^1$ can represent a silyl group of the formula Si(R'$_2$)R wherein R' is a lower alkyl residue of up to four carbon atoms. However, $R^1$ can also be an alkyl group of up to seven carbon atoms, an aralkyl group of 7-9 carbon atoms, an acyl residue of 2-5 carbon atoms, or an arylsulfonyl residue, such as the p-toluenesulfonyl residue.

Alkyl residues of up to seven carbon atoms are, besides the above-cited lower alkyl residues, for example, n-pentyl, n-hexyl, 1-methylpentyl and 2,2-dimethylbutyl. Aralkyl groups are, for example, benzyl and phenethyl. Acyl groups of 2-5 carbon atoms are derived from aliphatic carboxylic acids, such as acetic acid, propionic acid, butyric acid, caproic acid and trimethylacetic acid.

Low temperatures include temperatures below 0° C., especially those in the range from −110° to −70° C. These temperatures are attained, for instance, by the use of solid carbon dioxide or liquid nitrogen in methanol, ether, or similar solvents as the coolants.

Suitable as solvents for the reaction are those showing inert behavior under the aforementioned reaction conditions, for example, aliphatic and aromatic hydrocarbons, such as hexane and toluene, or ethers, such as tetrahydrofuran, dioxane and diethyl ether. The addition of a stoichiometric quantity of tetramethylenediamine, based on the alkyllithium, is advantageous. The reaction is completed after a short period of time, i.e., after about 2-10 minutes.

The 2-lithium ergoline derivative of formula IV prepared by the above reaction is stable at low temperatures. The reaction solution need not be given further work up and is used directly in the subsequent reaction stage. In this reaction stage, the 2-lithium ergoline derivative is reacted in an inert solvent with an electrophilic reagent, including carbon dioxide, ethylene oxide, methyl isocyanate, methyl thioisocyanate, lower alkyl chlorosilane, lower alkyl and lower alkenyl bromide or iodide and including alkyl disulfides, such as dimethyl disulfide or tetraisopropylthiuram disulfide, at low temperatures in the range from −110° to −50° C.

Where the reactant is a gas, then the latter is piped in or is made to react with the 2-lithium ergoline derivative in the solid phase, as solid carbon dioxide, for example, and in a pressure vessel.

If the substituent in the 2-position represents a free carboxy function, then the latter can be esterified, if desired, by conventional methods such as reacting the ergoline with an aliphatic alcohol of the formula ROH wherein R is a $C_{1-4}$-alkyl residue. For example, the ergoline-2-carboxylic acid can be reacted with the alcohol in the presence of an inorganic acid, such as hydrochloric or perchloric acid, at room temperature, to produce the ergolinyl ester.

Conventional methods are likewise employed for preparing compounds of Formula I wherein $R^2$ is
the grouping COR' or CSR' wherein R' is OH, OC$_{1-4}$-alkyl, benzyl, NH$_2$ or NHR";
the grouping CH=CH—CO$_2$R" or CH$_2$—CH$_2$—CO$_2$R" wherein R" is $C_{1-4}$-alkyl;
the grouping C≡C—R''' and HC=CH—R''' wherein R''' is hydrogen, $C_{1-4}$-alkyl, phenyl, CH$_2$OH, CR"$_2$OH,

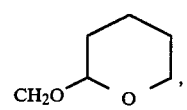

CO$_2$R", CH$_2$NR"$_2$, SiMe$_2$R"; or

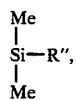

wherein R" means lower alkyl of up to 4 carbon atoms.

For this purpose, a 2-iodo- or 2-bromoergoline of Formula V

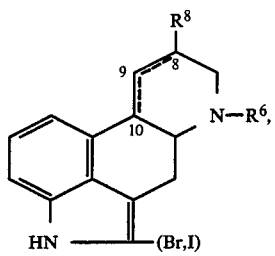

wherein
$C_8 --- C_9$, $C_9 --- C_{10}$, $R^6$ and $R^8$ have the meanings given above, is reacted with an electrophilic reagent, such as benzyl alcohol under a carbon monoxide atmosphere, an acrylic ester ($CH_2=CH-CO_2R''$) or a monosubstituted acetylene ($CH\equiv CR'''$), in the presence of a palladium catalyst and a secondary or tertiary amine, without a solvent or in an aprotic water-miscible solvent, at temperatures of above room temperature in the range from 40° C. to the boiling temperature of the reaction mixture; and optionally, subsequently, the 2-benzyl gorup is hydrogenated with palladium with formation of the carboxy compound, or is reacted with ammonia to the 2-carboxylic acid amide group; or an exocyclic multiple bond is hydrogenated with Raney nickel or palladium on a support to the CC-single bond or double bond; or a $SiMe_2R''$-blocking group is split off with a base or a tetrahydropyranyl blocking group is split off with pyridinium p-toluenesulfonate, Monosubstituted acetylene refers to ethynyl derivatives wherein an H-atom is substituted by $C_{1-3}$-alkyl, phenyl, hydroxymethyl, tetrahydropyranyloxy, $C_{1-3}$-alkoxycarbonyl, di-$C_{1-3}$-alkylaminomethyl or $C_{1-3}$-alkyl dimethylsilyl. Acrylic esters have 1–3 C-atoms in the alcohol portion.

The reaction with the acrylic ester or the acetylenic compound may be performed in the absence of solvent, in the corresponding amine, or in an aprotic, water-miscible solvent in the presence of a secondary or tertiary amine.

Secondary and tertiary amines include, for example, dimethylamine, diethylamine, piperidine, triethylamine and tri-n-butylamine. Aprotic, water-miscible solvents include dimethylformamide, N-methylpyrrolidone tetrahydrofuran, acetonitrile and dioxane. The reaction is performed at temperature above room temperature in the range from 40° C. to the boiling temperature of the reaction mixture. The reaction is additionally performed in the presence of a palladium catalyst.

Suitable palladium catalysts are palladium salts and palladium complex compounds, e.g., palladium(II) acetate, trans-dichlorobis(tri-o-tolylphosphine) palladium-(II), trans-dichlorobis(triphenylphosphine) palladium-(II) and palladium(O) tetrakistriphenylphospine. The catalyst is used in an amount of 0.01–0.1 mole, based on the 2-haloergoline that is used.

In some reactions, an addition of copper(I) iodide or of tri-o-tolylphosphine proved to be advantageous.

The reactions are performed in the absence of air and often under elevated pressure, e.g., in an inert gas atmosphere and in an autoclave.

Where the substituent R' means hydroxy, then the corresponding 2-carboxylic acid benzyl ester is hydrogenated under normal pressure at room temperature in a protonic solvent, such as an aliphatic alcohol, e.g., methanol, in the presence of finely divided palladium, such as palladium black.

Where the substituent R' means an amino group, then the corresponding 2-benzyl ester is reacted with the corresponding carboxylic acid amide and ammonia at elevated temperatures and in a protonic solvent such as an alcohol, preferably ethylene glycol.

Where the substituent in the 2-position contains an exocyclic C=C double bond or C≡C-triple bond, the unsaturated bond can be readily entirely or partially reduced, e.g., with Raney nickel or palladium on carbon to the corresponding hydrogenation product. The reduction is performed in an aliphatic alcohol at room temperature under normal pressure.

Where the ethynyl substituent in the 2-position contains a blocking group, such as an $SiMe_2R''$-group, then this group can be removed at room temperature with a weak base, such as sodium or potassium carbonate. The blocking group can also be removed with acids or fluoride ions, e.g., cesium fluoride or tetrabutylammonium fluoride. If the ethynyl group is blocked unilaterally as an acetone addition product, then the blocking group can be removed by boiling at 100° C. with a strong base, such as potassium or sodium hydroxide.

Where the blocking group is the tetrahydropyranyl residue, the removal step is conducted at 70°–100° C. in an acid solution such as pyridinium p-toluenesulfonate or dilute sulfuric acid in an alcohol.

The resultant compounds of Formula I are purified by recrystallization and/or chromatography either as the free bases or, if desired, in the form of their acid addition salts. The salts may be obtained by reaction with a physiologically compatible acid such as tartaric acid or maleic acid. For the formation of salts, the compounds of Formula I are dissolved in a small amount of methanol or methylene chloride and combined at room temperature with a concentrated solution of the desired acid in methanol.

The starting compounds necessary for performing the process of this invention are either known or can be prepared according to methods known to a person skilled in the art. Some sample preparations follow.

Preparation of the Starting Materials

A solution is prepared from 1 mmol of terguride in 20 ml of anhydrous dioxane, combined with about 1.5 ml of N-iodosuccinimide at room temperature and stirred for 30 minutes. The reaction mixture is then poured into a saturated bicarbonate solution, extracted with methylene chloride and the organic phase is dried with magnesium sulfate. After evaporation of the solvent, the residue is chromatographed on silica gel, thus obtaining in a 76% yield 1,1-diethyl-3-(2-iodo-6-methyl-8α-ergolinyl)urea.

$[\alpha]_D = +37.3°$ c=0.2 in pyridine.

Analogously, lisuride and N-bromosuccinimide yield 1,1-diethyl-3-(2-bromo-6-methyl-9,10-didehydro-8α-ergolinyl)urea (23%).

$[\alpha]_D = +247°$ c=0.2 in pyridine.

In a likewise analogous way, lisuride and N-iodosuccinimide yield 1,1-diethyl-3-(2-iodo-6-methyl-9,10-didehydro-8α-ergolinyl)urea (20%).

Under ice cooling, a solution of lithium diisopropylamide is prepared from 27 ml of 15% strength n-butyllithium in hexane (67 mmol), 9.1 ml of anhydrous diisopropylamine and 40 ml of anhydrous tetrahydrofuran.

This solution is cooled to −20° C. and a solution of 12.7 g of bromoagroclavine (30 mmol) in 115 ml of anhydrous tetrahydrofuran is added dropwise thereto; the mixture is agitated at this temperature for 15 minutes and then 7.3 ml of tert-butyldimethylsilyl chloride (48 mmol) in 15 ml of anhydrous tetrahydrofuran is added thereto. This mixture is allowed to heat up to room temperature and agitated for 2 days. The mixture is distributed between ethyl acetate and bicarbonate solution; the organic phase is dried over sodium sulfate and evaporated. The residue is chromatographed on silica gel with methylene chloride, then with methylene chloride/methanol, yielding 2-bromo-1-(tert-butyldimethylsilyl)-8,9-didehydro-6,8-dimethylergoline in an 83% yield.

$[\alpha]_D = -161°$ (0.5% in chloroform).

The following compounds are produced analogously:

3-[2-bromo-1-(tert-butyldimethylsilyl)-9,10-didehydro-6-methyl-8α-ergolinyl]-1,1-diethylurea, yield: 72% of theory;

3-[2-bromo-1-(tert-butyldimethylsilyl)-6-methyl-8α-ergolinyl]-1,1-diethylurea, yield: 63% (from diisopropyl ether), $[\alpha]_D = +6°$ (0.5% from chloroform);

3-[2-bromo-1-(tert-butyldiphenylsilyl)-9,10-didehydro-6-methyl-8α-ergolinyl]-1,1-diethylurea; yield: 29%, $[\alpha]_D = +183°$ (0.5% in chloroform);

3-[2-bromo-1-(tert-butyldiphenylsilyl)-6-methyl-8α-ergolinyl]-1,1-diethylurea, yield: 19%, $[\alpha]_D = -0.6°$ (0.5% in chloroform);

3-[2-bromo-1-(tert-butyldimethylsilyl)-9,10-didehydro-6-methyl-8α-ergolinyl]-1,1-diethylthiourea;

3-[2-bromo-1-(tert-butyldimethylsilyl)-6-methyl-8α-ergolinyl]-1,1-diethylthiourea;

3-[2-bromo-1-(tert-butyldimethylsilyl)-6-methyl-8β-ergolinyl]-1,1-diethylurea, yield: 65%, $[\alpha]_D = -80°$ (0.5% in chloroform);

3-[2-bromo-1-(tert-butyldimethylsilyl)-n-propyl-8α-ergolinyl]-1,1-diethylurea, yield: 77%, $[\alpha]_D = -5°$ (0.5% in chloroform).

2.7 g of bromoagroclavine (8.5 mmol) is dissolved in 400 ml of methylene chloride; 0.4 g of tetrabutylammonium hydrogen sulfate, 2.1 g of pulverized potassium hydroxide and 2.1 ml of trimethylacetic acid chloride are added, and the mixture is stirred for 30 minutes at room temperature. Then ice is added, the mixture is again stirred for 30 minutes at room temperature and extracted with bicarbonate solution and additional methylene chloride. After evaporation an chromatography on silica gel with methylene chloride and methanol, 2.6 g of 2-bromo-8,9-didehydro-6,8-dimethyl-1-(trimethylacetyl)ergoline is obtained (76% of theory).

$[\alpha]_D = -104°$ (0.5% in chloroform).

The following acyl compounds are prepared in an analogous way:

2-bromo-8,9-didehydro-6,8-dimethyl-1-(tert-butoxycarbonyl)ergoline, yield: 69%; $[\alpha]_D = -121°$ (0.5% in chloroform);

2-bromo-8,9-didehydro-6,8-dimethyl-1-(4-methoxy-2,3,6-trimethylphenylsulfonyl)ergoline; yield: 74% (after chromatography) and 41% (after recrystallization from methanol), respectively, $[\alpha]_D = -142°$ (0.5% in chloroform);

2-bromo-8,9-didehydro-6,8-dimethyl-1-(2,4,6-trimethoxyphenylsulfonyl)ergoline, yield: 81% (from methanol).

The invention furthermore relates to a novel process for producing 2-(trialkylsilyl)ergoline derivatives of Formula I, a 2-bromo-1-(trialkylsilyl)ergoline of general Formula VI

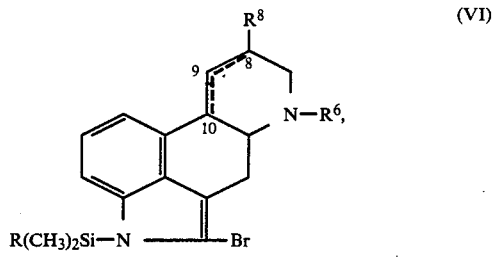

wherein $C_8 --- C_9$, $C_9 --- C_{10}$, R, $R^6$ and $R^8$ have the above meanings, is reacted with an alkyllithium at temperatures of below 0° C., optionally in the presence of a tertiary amine, when $R^2$ in Formula I is the grouping

wherein $R'' = C_{1-4}$-alkyl and is subsequently, if desired, converted into the acid addition salt with a physiologically compatible acid.

2-(trialkylsilyl)ergoline derivatives can be prepared per se by electrophilic substitution of compounds metallized in the 2-position. This novel procedure has not been disclosed heretofore in connection with ergoline derivatives; however, the process shows only unsatisfactory yields. It is an additional object of the present invention to provide a process for preparation of 2-(trialkylsilyl)ergoline derivatives which affords better yields.

It has now been found surprisingly that the preparation of 2-(trialkylsilyl)ergoline derivatives is highly successful if 2-bromo-1-trialkylsilyl)ergoline derivatives are reacted in a cyclic ether with an alkyllithium, and the product is rearranged to the corresponding 2-(trialkylsilyl)ergoline compound. The process of this invention is conducted by reacting the 2-bromo-1-(trialkylsilyl)ergoline at low temperatures, e.g., below 0° C., especially −70° to −20° C. These temperatures can be obtained by using coolants such as solid carbon dioxide in methanol and/or methylene chloride. Cyclic ethers are used as a solvent, preferably tetrahydrofuran and dioxane. The solvent is used in great excess, preferably in about 10–500 fold quantity. An alkyllithium is added to the reaction mixture in an amount of 1–5 equivalents and the product is rearranged after a prolonged reaction period into the corresponding 2-silylergoline derivative. Tertbutyllithium is especially suitable as the alkyllithium. Depending on the chemical structure of the ergoline employed as the starting material, a tertiary amine, such as tetramethylethylenediamine, can be added to the reaction mixture. The isomerization is terminated after a few hours, i.e., after 2–8 hours.

The course of the process according to this invention is surprising insofar as the rearrangement reaction does not occur in other solvents customary in silylation reactions, such as toluene or benzene.

The following example demonstrates this fact.

800 mg of 2-bromo-1-(tert-butyldimethylsilyl)-8,9-didehydro-6,8-dimethylergoline was dissolved in 50 ml of anhydrous toluene; the solvent was distilled off under vacuum and the mixture taken up in 75 ml of anhydrous, freshly distilled toluene under an argon atmosphere. To this solution was added 1 ml of anhydrous tetramethylethylenediamine and the mixture was cooled to −90° C. Then the mixture was combined with 6.0 ml of 1.4-molar tert-butyllithium solution in hexane (8.4 mmol) and agitated for 5 hours. Water was then added, the mixture was extracted with methylene chloride, the organic phase was dried with sodium sulfate and evaporated. In a quantitative yield, 8,9-didehydro-6,8-dimethylergoline was isolated. The desired 8,9-didehydro-6,8-dimethyl-2-trimethylsilylergoline could not be detected by NMR.

The starting compounds needed for conducting the process of this invention are either known or can be prepared according to methods known to those skilled in the art. For example "Die Mutterkornalkaloide" by A. Hoffmann, Enke-Verglag Stuttgart, 1964, and "Lisuride and Other Agonists" by D. B. Calne, R. Horowski, R. G. McDonald and W. Wuttke, Raven Press, NY, 1983.

Under ice cooling, a solution of lithium diisopropylamide is prepared from 27 ml of 15% n-butyllithium in hexane (67 mmol), 9.1 ml of anhydrous diisopropylamine and 40 ml of anhydrous tetrahydrofuran. This solution is cooled to −20° C. and a solution of 12.7 g of bromoagroclavine (30 mmol) in 115 ml of anhydrous tetrahydrofuran is added dropwise thereto; the mixture is agitated for 15 minutes at this temperature, and then 7.3 ml of tert-butyldimethylsilyl chloride (48 mmol) in 15 ml of anhydrous tetrahydrofuran is added thereto. This mixture is allowed to heat up to room temperature and agitated for 2 days. The mixture is distributed between ethyl acetate and bicarbonate solution, the organic phase is dried over sodium sulfate and evaporated. The residue is chromatographed on silica gel with methylene chloride, then with methylene chloride/methanol. Yield: 2-bromo-1-(tert-butyldimethylsilyl)-8,9-didehydro-6,8-dimethylergoline, the starting material of the previous example, in an 83% yield, $[\alpha]_D = -161°$ (0.5% in chloroform).

The following compounds are produced analogously:
3-[2-bromo-1-(tert-butyldimethylsilyl)-9,10-didehydro-6-methyl-8α-ergolinyl]-1,1-diethylurea, yield: 72% of theory;
3-[2-bromo-1-(tert-butyldimethylsilyl)-6-methyl-8α-ergolinyl]-1,1-diethylurea, yield: 63% (frm diisopropyl ether), $[\alpha]_D = +6°$ (0.5% from chloroform);
3-[2-bromo-1-(tert-butyldimethylsilyl)-9,10-didehydro-6-methyl-8α-ergolinyl]-1,1-diethylthiourea;
3-[2-bromo-1-(tert-butyldimethylsilyl)-6-methyl-8α-ergolinyl]-1,1-diethylthiourea;
3-[2-bromo-1-(tert-butyldimethylsilyl)-6-methyl-8β-ergolinyl]-1,1-diethylurea, yield: 65%, $[\alpha]_D = -80°$ (0.5% in chloroform); and
3-[2-bromo-1-(tert-butyldimethylsilyl)-n-propyl-8α-ergolinyl]-1,1-diethylurea, yield: 77%, $[\alpha]_D = -5°$ (0.5% in chloroform).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

680 mg of terguride (2 mmol) is dissolved in 120 ml of acetonitrile and 5.5 ml of triethylamine and, under ice cooling, a solution of 3.5 ml of chlorosulfonyl isocyanate in 40 ml of acetonitrile is added dropwise thereto under an argon atmosphere. The ice bath is removed and the mixture allowed to stand for two days at room temperature. To facilitate isolation of the polar by-products, the mixture is combined with 20 ml of diethylamine and stirred for three hours at room temperature. Then the mixture is diluted with methylene chloride, extracted with 1N sodium hydroxide solution, and the water phase is once more extracted. The combined organic phases are dried with sodium sulfate and evaporated. The residue is chromatographed on silica gel with a mixture of methylene chloride and methanol, thus isolating 229 mg (31% of theory) of crude 3-(2-cyano-6-methyl-8α-ergolinyl)-1,1-diethylurea. Ater crystallizing from ethyl acetate, 92 mg is obtained as the pure compound.
$[\alpha]_D = +20°$ (0.1% in chloroform)

The polar by-products are acylation products in the 1- and/or 2-position.

EXAMPLE 2

507 mg of lisuride (1.5 mmol) is dissolved in 30 ml of tetrahydrofuran and, at room temperature under nitrogen, 588 mg of dimethylmethylthiosulfonium fluoborate (3 mmol) is added. After 30 minutes of agitation at room temperature, the mixture is distributed between methylene chloride and bicarbonate solution, the organic phases are combined, dried with sodium sulfate and evaporated. The crude product is chromatographed on silica gel with methylene chloride and methanol; the yield is 506 mg (82% of theory) of 3-(9,10-didehydro-6-methyl-2-methylthio-8α-ergolinyl)-1,1-diethylurea, from which the tartrate is produced.

Yield: 208 mg (55% of theory); $[\alpha]_D = +226°$ (0.5% in pyridine).

The following compounds are prepared analogously:
From terguride
1,1-diethyl-3-(6-methyl-2-methylthio-8α-ergolinyl)urea, yield: 58% (after chromatography), tartrate (79% yield): $[\alpha]_D = +23°$ (0.5% in pyridine).
From 8,9-didehydro-6,8-dimethylergoline 8,9-didehydro-6,8-dimethyl-2-methylthioergoline, yield: 95% (after chromatography), tartrate (40% yield): $[\alpha]_D = -172°$ (0.1% in pyridine).
From 3-(6-methyl-8α-ergolinyl)-1,1-diethylthiourea 1,1-diethyl-3-(6-methyl-2-methylthio-8α-ergolinyl)-thiourea, yield: 26%, $[\alpha]_D = +54°$ (0.5% in chloroform).
From 1,1-diethyl-3-(6-methyl-8β-ergolinyl)urea 1,1-diethyl-3-(6-methyl-2-methylthio-8β-ergolinyl)urea, $[\alpha]_D = -100°$ (0.1% in chloroform), yield: 47%.
From 1,1-diethyl-3-(6-n-propyl-8α-ergolinyl)urea 1,1-diethyl-3-(2-methylthio-6-n-propyl-8α-ergolinyl)urea, yield: 62%, $[\alpha]_D = +7°$ (0.5% in chloroform).

EXAMPLE 3

Under ice cooling, 3 ml (42 mmol) of acetyl chloride is combined with 0.467 g (3.5 mmol) of anhydrous aluminum chloride and, at −10° C., with 0.477 g (1.4 mmol) of 3-(6-methyl-8α-ergolinyl)-1,1-diethylurea. After 2.5 hours of agitation at −5° to 0° C., 30 ml of hexane is added and the mixture decanted from the oily sediment, which latter is taken up in methylene chloride/water. The organic phase is washed with 10% sodium bicarbonate solution and with saturated sodium chloride solution, dried over magnesium sulfate and concentrated. Column chromatography over 150 g of silica gel with methylene chloride/ethanol 10:1 and recrystallization from ethanol/hexane yield 134 mg (25%) of 3-(2-acetyl-6-methyl-8α-ergolinyl)-1,1-diethylurea, mp 114°–116° C.

$[\alpha]_D = +51°$ (0.2% in pyridine).

The following compounds are produced in an analogous way:

2-acetyl-8,9-didehydro-6,8-dimethylergoline (mp 168°–169° C.), ethanol/hexane, from 8,9-didehydro-6,8-dimethylergoline;

3-(2-propionyl-6-methyl-8α-ergolinyl)-1,1-diethylurea from terguride; and 3-(2-acetyl-9,10-didehydro-6-methyl-8α-ergolinyl)-1,1-diethylurea from lisuride.

EXAMPLE 4

57 mg (0.149 mmol) of 3-(2-acetyl-6-methyl-8α-ergolinyl)-1,1-diethylurea in 4 ml of absolute tetrahydrofuran is heated under reflux for 2 hours with 38 mg (1 mmol) of sodium borohydride and 18 mg (0.162 mmol) of anhydrous calcium chloride. After cooling to room temperature and addition of water, the mixture is stirred for 10 minutes, the tetrahydrofuran is removed by distillation, and the mixture is combined with methylene chloride. Washing of the organic phase with saturated sodium chloride solution and drying over magnesium sulfate yield, after concentration and column chromatographing of the crude product over 75 g of silica gel with methylene chloride/ethanol=5:1, 26 mg (46.6%) of 3-[2-(1-hydroxyethyl)-6-methyl-8α-ergolinyl]-1,1-diethylurea as an oil that is crystallized throughout; mp starting with 175° C.

The following compounds are prepared analogously:
From 3-(2-acetyl-9,10-didehydro-6-methyl-8α-ergolinyl)-1,1-diethylurea; 3-[2-(1-hydroxyethyl)-9,10-didehydro-6-methyl-8α-ergolinyl]-1,1-diethylurea, from 3-(2-propionyl-6-methyl-8α-ergolinyl)-1,1-diethylurea, 3-[2-(1-hydroxypropyl)-6-methyl-8α-ergolinyl]-1,1-diethylurea, and from 2-acetyl-8,9-didehydro-6,8-dimethylergoline, 2-(1-hydroxyethyl)-8,9-didehydro-6,8-dimethylergoline.

EXAMPLE 5

210 mg of 1,1-diethyl-3-(6-methyl-2-methylthio-8α-ergolinyl)urea is dissolved in 20 ml of acetonitrile, and 0.5 g of sodium metaperiodate in 5 ml of water is added thereto in incremental portions. The mixture is stirred at 50° C. for 16 hours, the residue is distributed between methylene chloride and water, the organic phase is dried with sodium sulfate and evaporated. The residue is chromatographed on silica gel. Yield: 109 mg of 1,1-diethyl-3-(6-methyl-2-methylsulfinyl-8α-ergolinyl)urea.

$[\alpha]_D = +13°$ (0.5% in chloroform).

EXAMPLE 6

800 mg of 3-[2-bromo-1-(tert-butyldimethylsilyl)-6-methyl-8α-ergolinyl]-1,1-diethylurea (1.5 mmol) is dissolved in 50 ml of anhydrous toluene, the solvent is distilled off under vacuum, and the mixture is taken up with 75 ml of anhydrous, freshly distilled toluene under an argon atmosphere. To this solution is added 1 ml of anhydrous tetramethylethylenediamine and the mixture is cooled to −90° C. Then the mixture is combined with 6.0 ml of 1.4-molar tert-butyllithium solution in hexane (8.4 mmol) and stirred for 2 minutes, thus obtaining a soltion of 3-[1-(tert-butyldimethylsilyl)-2-lithium-6-methyl-8α-ergolinyl]-1,1-diethylurea, which is used in the subsequent stage.

The thus-prepared solution of the 2-lithium ergoline is combined with a solution of 0.6 ml of methyl isocyanate (9 mmol) in 4 ml of toluene and stirred for 30 minutes at −70° C. Then water is added, the mixture is extracted with methylene chloride, the organic phase is dried with sodium sulfate and evaporated. The residue is chromatographed on silica gel with methylene chloride and methanol, thus isolating 142 mg of 8α-(3,3-diethylureido)-6-methylergoline-2-carboxylic acid methylamide (24% of theory). Crystallization from methylene chloride and diisopropyl ether yields 87 mg (15% of theory).

$[\alpha]_D = +50°$ (0.2% in pyridine).

The following compounds are produced analogously:

9,10-didehydro-8α-(3,3-diethylureido)-6-methylergoline-2-carboxylic acid methylamide, yield: 16%, $[\alpha]_D = +284°$ (0.1% in pyridine);

8,9-didehydro-6,8-dimethylergoline-2-carboxylic acid methylamide, yield: 51%, $[\alpha]_D = -162°$ (0.5% in chloroform).

By replacing methyl isocyanate by methyl isothiocyanate, the following compounds are obtained:

8α-(3,3-diethylureido)-6-methylergoline-2-thiocarboxylic acid methylamide, yield: 52%, $[\alpha]_D = +22°$ (0.2% in pyridine);

9,10-didehydro-8α-(3,3-diethylureido)-6-methylergoline-2-thiocarboxylic acid methylamide, yield: 22%, $[\alpha]_D = +319°$ (0.1% in pyridine);

8,9-didehydro-6,8-dimethylergoline-2-thiocarboxylic acid methylamide, yield: 58%, $[\alpha]_D = -328°$ (0.2% in pyridine).

By using trimethylsilyl isocyanate in place of methyl isocyanate:

8α-(3,3-diethylureido)-6-methylergoline-2-carboxylic acid amide, yield: 47%; $[\alpha]_D = +42°$ (0.2% in pyridine).

With the trimethylsilyl ester of trifluoromethylsulfonic acid in place of methyl isocyanate:

8,9-didehydro-6,8-dimethyl-2-trimethylsilylergoline, yield: 15% $[\alpha]_D = -177°$ (0.5% in chloroform), and 1,1-diethyl-3-(6-methyl-2-trimethylsilyl-8α-ergolinyl)urea, yield: 35%; $[\alpha]_D = +30°$ (0.5% in chloroform).

With methyl iodide in place of methylisocyanate:
3-(2,6-dimethyl-8α-ergolinyl)-1,1-diethylurea.

With carbon dioxide in place of methyl isocyanate:
A solution of 2-lithium ergoline prepared as described above is quickly poured on maximally dry, solid $CO_2$. The mixture is sealed into a pressure vessel where it is heated up to room temperature. Next morning, the vessel is gently opened and the content worked up as usual. The reaction product is purified by chromatography.

8,9-didehydro-6,8-dimethylergoline-2-carboxylic acid, yield: 60%, $[\alpha]_D = -152°$ (0.1% in pyridine);

9,10-didehydro-8α-(3,3-diethylureido)-6-methylergoline-2-carboxylic acid, yield: 42%, $[\alpha]_D = +187°$ (0.2% in methanol);

8α-(3,3-diethylureido)-6-methylergoline-2-carboxylic acid, yield: 48%, $[\alpha]_D = +27°$ (0.2% in methanol).

By replacement of methyl isocyanate with dimethyl disulfide:

1,1-diethyl-3-(6-methyl-2-methylthio-8α-ergolinyl)urea, yield: 67%; from this, the tartrate in an 80% yield. $[\alpha]_D = +23°$ (0.5% in pyridine).

With tetraisopropylthiuram disulfide:

8,9-didehydro-6,8-dimethylergolin-2-yl-(N,N-diisopropyl)dithiocarbamate, yield: 65%; $[\alpha]_D = -144°$ (0.5% in chloroform); bis-[8α-(3,3-diethylureido)-6-methyl-2-ergolinyl]disulfide.

EXAMPLE 7

Esterification of the free ergoline-2-carboxylic acids obtained in Example 6 with methanol yields the respective methyl esters by allowing the mixture to stand at room temperature in methanolic hydrochloric acid:

8,9-didehydro-6,8-dimethylergoline-2-carboxylic acid methyl ester, yield: 42%, $[\alpha]_D = -266°$ (0.5% in chloroform);

9,10-didehydro-8α-(3,3-diethylureido)-6-methylergoline-2-carboxylic acid methyl ester, yield: 46%, tartrate, yield: 57%, $[\alpha]_D = +217°$ (0.1% in pyridine);

8α-(3,3-diethylureido)-6-methylergoline-2-carboxylic acid methyl ester, yield: 50%, tartrate, yield: 60%, $[\alpha]_D = +33°$ (0.1% in pyridine).

EXAMPLE 8

Under an argon atmosphere, 730 mg of 2-bromo-8,9-didehydro-6,8-dimethyl-1-(trimethylacetyl)ergoline (1.5 mmol) is dissolved in 60 ml of anhydrous toluene, 1 ml of anhydrous tetramethylethylenediamine is added to this solution, and the latter is cooled to $-90°$ C. Then the mixture is combined with 1.4 ml of tert-butyllithium solution in hexane (8.4 mmol) and stirred for 2 minutes. The resultant solution of 8,9-didehydro-6,8-dimethyl-2-lithium-1-trimethylacetylergoline is quickly poured on dry, solid carbon dioxide and sealed into a pressure vessel. Next morning, the vessel is gently opened and the reaction mixture worked up as usual, thus obtaining 8,9-didehydro-6,8-dimethylergoline-2-carboxylic acid in a 51% yield. $[\alpha]_D = -151°$ (0.1% in pyridine).

EXAMPLE 9

As described in Example 6, 3-[2-bromo-1-(tert-butyldimethylsilyl)-6-methyl-8β-ergolinyl]-1,1-diethylurea and tert-butyllithium are employed to produce the corresponding 2-lithium compound. The latter is reacted with dimethyl disulfide, instead of with methyl isocyanate, thus producing 1,1-diethyl-3-(6-methyl-2-methylthio-8β-ergolinyl)urea, yield: 54%. $[\alpha]_D = -100°$ (0.1% in methanol).

EXAMPLE 10

Analogously to Example 6, 3-[2-bromo-1-(tertbutyldimethylsilyl)-6-n-propyl-8α-ergolinyl]-1,1-diethyl urea yields, with tert-butyllithium, the corresponding lithium compound, and from the latter, using dimethyl disulfide, 1,1-diethyl-3-(2-methylthio-6-n-propyl-8α-ergolinyl)urea is prepared.

Yield: 51%; $[\alpha]_D = +6°$ (0.5% in chloroform).

EXAMPLE 11

300 mg (0.644 mmol) of 3-(2-iodo-6-methyl-8α-ergolinyl)-1,1-diethylurea is heated, after adding 0.169 ml (0.709 mmol) of tri-m-butylamine, in 4 ml of benzyl alcohol, combined under a carbon monoxide atmosphere with 7 mg (0.031 mmol) of palladium(II) acetate, and kept at 100°–110° C. for 2.5 hours under vigorous agitation. After cooling to room temperature, the reaction solution is diluted with ethyl acetate and extracted with saturated sodium bicarbonate solution and saturated sodium chloride solution. After drying over magnesium sulfate, the ethyl acetate is removed by distillation under reduced pressure and then the benzyl alcohol is distilled off under a high vacuum. By column chromatography on 150 g of silica gel in a system of dichloromethane/ethanol = 10:1 and recrystallization from ethanol/hexane, 166 mg of 8α-(3,3-diethylureido)-6-methylergoline-2-carboxylic acid benzyl ester is produced from the crude product (54.5%), mp 226°–229° C.

$[\alpha]_D = +43.2°$ (c=0.25% in pyridine).

EXAMPLE 12

104 mg (0.22 mmol) of 8α-(3,3-diethylureido)-6-methylergoline-2-carboxylic acid benzyl ester is dissolved in 20 ml of methanol and, after adding 50 mg of palladium black, hydrogenated for 30 minutes under normal pressure at room temperature. After the catalyst has been filtered off and the mixture concentrated, 8α-(3,3-diethylureido)-6-methylergoline-2-carboxylic acid is obtained in a 100% yield, mp: decomposition starting with 230° C.

EXAMPLE 13

150 mg (0.31 mmol) of 8α-(3,3-diethylureido)-6-methylergoline-2-carboxylic acid benzyl ester is heated in 3 ml of a saturated solution of ammonia in ethylene glycol for 3 hours to 100° C. After dilution with water, the mixture is extracted with ethyl acetate and the organic phase washed with saturated sodium chloride solution, dried over magnesium sulfate, filtered, and concentrated. The residue is chromatographed over silica gel with methylene chloride/ethanol = 8:1. After trituration in ethanol/hexane/ether, 90 mg of 8α-(3,3-diethylureido)-6-methylergoline)-2-carboxylic acid amide is obtained, mp 171°–173° C.

$[\alpha]_D = +42.5°$ (c=0.2% in pyridine).

EXAMPLE 14

A solution is prepared from 261 mg (0.56 mmol) of 3-(2-iodo-6-methyl-8α-ergolinyl)-1,1-diethylurea, 7.0 mg (0.023 mmol) of tri-o-tolyl phosphine, 4.7 mg (0.006 mmol) of trans-dichlorobis(tri-o-tolyl phsophine) palladium(II) and 0.075 ml (0.69 mmol) of ethyl acrylate in 1.5 ml of dimethylformamide and 0.7 ml of triethylamine; after purging with argon, the solution is heated in an autoclave for 4 hours to 100° C. After concentrating the reaction solution under reduced pressure, it is taken up in ethyl acetate and washed with saturated sodium chloride solution. The crude product obtained after drying of the ethyl acetate phase over magnesium sulfate and concentration of the solution is chromatographed over 150 g of silica gel with dichloromethane/ethanol 10:1 as the solvent, thus obtaining 3-(2-ethoxycarbonylvinyl-6-methyl-8α-ergolinyl)-1,1-diethylurea.

Yield: 115 mg (47%), mp: 223°–225° C. (ethanol/hexane), $[\alpha]_D = +115°$ (c=0.2% in pyridine).

EXAMPLE 15

A solution is prepared from 178 mg (0.406 mmol) of 3-[(2-ethoxycarbonylvinyl)-6-methyl-8α-ergolinyl)]-1,1-diethylurea in 20 ml of ethanol and, after adding 0.1 g of Raney nickel, hydrogenated for one hour at room temperature under normal pressure. After the catalyst has been removed by filtration, 86 mg of 3-[2-(2-ethoxycarbonylethyl)-6-methyl-8α-ergolinyl]-1,1-diethylurea is obtained (48%), mp 160°–161° C., by recrystallizing from ethyl acetate/hexane.

$[\alpha]_D = +22°$ (c=0.2% in pyridine).

EXAMPLE 16

933 mg (2.0 mmol) of 3-(2-iodo-6-methyl-8α-ergolinyl)-1,1-diethylurea is dissolved in a mixture of 5 ml of dimethylformamide and 10 ml of triethylamine and, after addition of 0.610 ml (4.4 mmol) of ethynyltrimethylsilane, 19 mg (0.1 mmol) of copper(I) iodide, and 47.2 mg (0.06 mmol) of trans-dichlorobis(tri-o-tolyl phosphine) palladium(II), heated for 3 hours under argon to 60° C. After concentration under reduced pressure and taking up of the residue in ethyl acetate/water, the organic phase is washed with saturated sodium chloride solution, dried over magnesium sulfate, and evaporated. Column chromatography over 150 g of silica gel with methylene chloride/ethanol 10:1 as the eluent yields 486 mg of 3-(2-ethynyltrimethylsilyl-6-methyl-8α-ergolinyl)-1,1-diethylurea (55.7%) as an oil.

The following compounds are produced analogously:

3-[6-methyl-2-[3-(tetrahydropyran-2-yloxy)propynyl]-8α-ergolinyl]-1,1-diethylurea, mp 188° C., $[\alpha]_D = +64°$ (c=0.2% in pyridine);

3-(2-propynyl-6-methyl-8α-ergolinyl)-1,1-diethylurea;

3-[2-(1-dimethylaminopropyn-3-yl)-6-methyl-8α-ergolinyl]-1,1-diethylurea;

1,1-diethyl-3-[2-(2-methoxy-1-propynyl)-6-methyl-8α-ergolinyl]urea, mp 211°–214° C., $[\alpha]_D = +68.0°$ (c=0.2% in pyridine);

1,1-diethyl-3-[2-(3-hydroxy-3-methyl-1-butynyl)-6-methyl-8α-ergolinyl]urea, mp starting with 132°–140° C., $[\alpha]_D = +67.8°$ (c=0.2% in pyridine);

1,1-diethyl-3-(2-phenylethynyl-6-methyl-8α-ergolinyl)urea, mp 240°–242° C., $[\alpha]_D = +107.5°$ (c=0.2% in pyridine).

2-[2-(1-carbethoxyethyn-2-yl)-6-methyl-8α-ergolinyl]-1,1-diethylurea;

3-(2-trimethylsilylethynyl-6-methyl-8β-ergolinyl)-1,1-diethylurea;

3-(2-trimethylsilylethynyl-6-methyl-8α-ergolinyl)-1,1-diethylthiourea;

3-(2-trimethylsilylethynyl-1,6-dimethyl-8α-ergolinyl)-1,1-diethylurea;

8,9-didehydro-6,8-dimethyl-2-phenylethynylergoline, mp starting with 118° C. (decomposition); and 3-(2-trimethylsilylethynyl-6-n-propyl-8α-ergolinyl)-1,1-diethylurea.

EXAMPLE 17

Starting with 3-(2-bromo-6-methyl-8α-ergolinyl)-1,1-diethylurea, 3-(tetrahydropyran-2-yloxy)-1-propyne yields 3-[9,10-didehydro-6-methyl-2-[3-(tetrahydropyran-2-yloxy)-1-propynyl]-8α-ergolinyl]-1,1-diethylurea (25%) and 3-hydroxy-3-methyl-1-butyne yields 3-[9,10-didehydro-2-(3-hydroxy-3-methyl-1-butynyl)-6-methyl-8α-ergolinyl]-1,1-diethylurea (31%).

EXAMPLE 18

262 mg (0.6 mmol) of 3-(2-ethynyltrimethylsilyl-6-methyl-8α-ergolinyl)-1,1-diethylurea is dissolved in a mixture of 9 ml of ethanol and 1 ml of water and, after the addition of 104 mg (0.75 mmol) of anhydrous potassium carbonate, stirred for 16 hours at room temperature. The solvent is removed by distillation, the mixture is taken up in ethyl acetate and extracted with saturated sodium chloride solution. After drying the ethyl acetate solution over magnesium sulfate, removing the solvent by distillation, and column chromatography of the crude product on 150 g of silica gel with toluene/ethanol/water in a ratio of 80:20:1 as the eluent, 81 mg of 3-(2-ethynyl-6-methyl-8α-ergolinyl)-1,1-diethylurea is obtained (37%) by recrystallization from ethanol/hexane, mp 192° C.

$[\alpha]_D = 60.6°$ (c=0.175% in pyridine).

The following compounds are prepared analogously:

3-(2-ethynyl-6-methyl-8α-ergolinyl)-1,1-diethylthiourea;

3-(2-ethynyl-1,6-dimethyl-8α-ergolinyl)-1,1-diethylurea; and 3-(2-ethynyl-6-n-propyl-8α-ergolinyl)-1,1-diethylurea, mp 126° C.

$[\alpha]_D = +65.9°$ (c=0.13% in pyridine).

EXAMPLE 19

Under nitrogen, 122 mg (0.29 mmol) of 3-[9,10-didehydro-2-(3-hydroxy-3-methyl-1-butynyl)-6-methyl-8α-ergolinyl]-1,1-diethylurea is heated for 2 hours under reflux in 15 ml of absolute toluene after adding 64 mg (1.6 mmol) of pulverized sodium hydroxide. The solvent is then removed by distillation and the residue extracted in ethyl acetate with water and saturated sodium chloride solution. The crude product obtained from the ethyl acetate solution after drying with magnesium sulfate and concentration is purified by column chromatography on 80 g of silica gel with ethyl acetate/ethanol 2:1 as the eluent. Reprecipitation from ethyl acetate/ether/hexane produces 3-(9,10-didehydro-2-ethynyl-8α-ergolinyl)-1,1-diethylurea in a 25% yield.

$[\alpha]_D = +34°$ (c=0.2% in pyridine).

EXAMPLE 20

213 mg (0.45 mmol) of 3-[6-methyl-2-[3-(tetrahydropyran-2-yloxy)propynyl]-8α-ergolinyl]-1,1-diethylurea is heated under reflux in 10 ml of ethanol with 2 ml of water and 176 mg (0.7 mmol) of pyridinium p-toluenesulfonate under argon for one hour. After evaporation and distribution in ethyl acetate and saturated bicarbonate solution, the organic phase is washed with saturated sodium chloride solution, dried over magnesium sulfate, filtered and concentrated. The residue is chromatographed over silica gel first with ethyl acetate/acetone=1:1 and later with methylene chloride/acetone=12:1. Recrystallization from ethyl acetate/hexane yields 90 mg (51%) of 3-[2-(1-hydroxypropyn-3-yl)-6-methyl-8α-ergolinyl]-1,1-diethylurea, mp 151°–154° C.

$[\alpha]_D = +71.2°$ (c=0.21% in pyridine).

The following compounds are prepared analogously:

3-[2-(1-hydroxypropyn-3-yl)-9,10-didehydro-6-methyl-8α-ergolinyl]-1,1-diethylurea, $[\alpha]_D = +404°$ (c=0.2 in pyridine), mp >129° C.

EXAMPLE 21

At room temperature and under normal pressure, 140 mg (0.084 mmol) of 3-(2-ethynyl-6-methyl-8α-ergolinyl)-1,1-diethylurea is hydrogenated in 20 ml of ethanol after addition of 0.1 g of Raney nickel within 45 minutes. After the catalyst has been removed by filtration and the solution has been concentrated, the product is recrystallized from ethanol/hexane, yielding 119 mg of 3-(2-ethyl-6-methyl-8α-ergolinyl)-1,1-diethylurea (84%), mp 165°–168° C., $[\alpha]_D = +25°$ (c=0.22 in pyridine).

The following compound is produced analogously:

1,1-diethyl-3-(6-methyl-2-phenethyl-8α-ergolinyl)urea, mp 175°–177° C.; $[\alpha]_D= +26°$ (c=0.1% in pyridine).

EXAMPLE 22

200 mg of 3-(2-ethynyl-6-methyl-8α-ergolinyl)-1,1-diethylurea is hydrogenated at room temperature and under normal pressure in 35 ml of ethanol with 200 mg of palladium/calcium carbonate (2%) and 200 mg of quinoline. After the mixture has been filtered off from the catalyst, it is evaporated. The residue is chromatographed over silica gel with methylene chloride/ethanol 6:1, thus obtaining 30 mg of 3-(6-methyl-2-vinyl-8α-ergolinyl)-1,1-diethylurea after recrystallization from ethanol/hexane, mp 145°–150° C.;

$[\alpha]_D= +63.5°$ (c=0.22% in pyridine).

EXAMPLE 23

800 mg of 3-[2-bromo-1-(tert-butyldimethylsilyl)-6-methyl-8α-ergolinyl]1,1-diethylurea (1.5 mmol) is dissolved in 75 ml of anhydrous, freshly distilled tetrahydrofuran under an argon atmosphere. To this solution is added 1 ml of anhydrous tetramethylethylenediamine, and the mixture is cooled to −80° C. (bath temperature). Then the mixture is combined with 6.0 ml of 1.4-molar tert-butyllithium solution in hexane (8.4 mmol), thus producing a solution of 3-[(1-tert-butyldimethylsilyl)-2-lithium-6-methyl-8α-ergolinyl)]-1,1-diethylurea which is stirred at −70° C. for 5 hours. After heating up to room temperature, water is added, the mixture is extracted with methylene chloride, the organic phase is dried with sodium sulfate and evaporated. The residue is chromatographed on silica gel with methylene chloride and methanol, thus isolating 265 mg of 3-[(2-tert-butyldimethylsilyl)-6-methyl-8α-ergolinyl)]-1,1-diethylurea (40% of theory).

$[\alpha]_D= +30°$ (0.5% in chloroform).

EXAMPLE 24

As described in Example 23, 1-(tert-butyldimethylsilyl)-2-bromo-8,9-didehydro-6,8-dimethylergoline is used to prepare, with tert-butyllithium, the 2-lithium compound in anhydrous tetrahydrofuran. This solution is stirred for 5 hours at −70° C., then worked up as usual and chromatographed. Yield: 65% of 2-(tert-butyldimethylsilyl)-8,9-didehydro-6,8-dimethylergoline.

$[\alpha]_D= -152°$ (0.5% in chloroform).

The following 2-silyl compounds are produced in the same way:

3-[2-(tert-butyldimethylsilyl)-6-methyl-8α-ergolinyl]-1,1-diethylthiourea,

3-[2-(tert-butyldimethylsilyl)-9,10-didehydro-6-methyl-8α-ergolinyl]-1,1-diethylurea, yield: 31%; $[\alpha]_D= +305°$ (0.5% in chloroform), 8,9-didehydro-6,8-dimethyl-2-trimethylsilylergoline, yield: 60%, $[\alpha]_D= -177°$ (0.5% in chloroform), 1,1-diethyl-3-(6-methyl-2-trimethylsilyl-8α-ergolinyl)urea, yield: 59%; $[\alpha]_D= +30°$ (0.5% in chloroform), 3-(9,10-didehydro-6-methyl-2-trimethylsilyl-8α-ergolinyl)-1,1-diethylurea, yield: 37%; $[\alpha]_D=317°$ (0.5% in chloroform), 3-(6-n-propyl-2-trimethylsilyl-8α-ergolinyl)-1,1-diethylurea, 3-(2-tert-butyldimethylsilyl)-6-methyl-8β-ergolinyl)-1,1-diethylurea.

EXAMPLE 25

At room temperature under argon, 7 ml of ethyl formate and 3.6 ml (44 mmol) of ethanedithiol are added in succession to a solution of 6.8 g of 1,1-diethyl-3-(6-methyl-8α-ergolinyl)urea in 200 ml of chloroform. Thereafter 8.8 ml (80 mmol) of titanium(IV) chloride dissolved in 100 ml of chloroform is added gradually dropwise to the mixture. The latter is stirred for 20 hours at room temperature. Although the starting material is not as yet entirely converted at this point in time, the reaction mixture is worked up to avoid further formation of the disubstituted compound. For this purpose, the reaction mixture is cooled in an ice bath and combined, in sequence, dropwise with 50 ml of methanol and 40 ml of water. The mixture is then made alkaline with 25% ammonia solution and extracted with methylene chloride. The organic phases are washed with water and dried over magnesium sulfate. The evaporated residue is crystallized in boiling heat from methanol/ethyl acetate, thus obtaining 3.8 g of 1,1-diethyl-3-[2-(1,3-dithiolan-2-yl)-6-methyl-8α-ergolinyl]urea (42% yield).

$[\alpha]_D= +29°$ (0.5% in CH$_3$OH).

EXAMPLE 26

7.5 ml of a Raney nickel suspension is washed four times with respectively 30 ml of methanol. Then 15 ml of methanol and thereafter a solution of 670 mg (1.5 mmol) of 1,1-diethyl-3-[2-(1,3-dithiolan-2-yl)-6-methyl-8α-ergolinyl]urea in 15 ml of methanol are added thereto. The mixture is agitated for 3 hours at room temperature and once again 7.5 ml of a Raney nickel suspension is added which has been washed, as above, previously four times with respectively 30 ml of methanol. After another 2 hours of agitation at room temperature, the catalyst is filtered off over a silica gel column and thoroughly washed with methanol. The filtrate is evaporated and the residue is crystallized from methanol/ethyl acetate, thus obtaining 170 mg of 1,1-diethyl-3-(2,6-dimethyl-8α-ergolinyl)urea (32% yield).

$[\alpha]_D= +12°$ (0.5% in CHCl$_3$).

EXAMPLE 27

2.05 g (5 mmol) of 1,1-diethyl-3-[2-(1,3-dithiolan-2-yl)-6-methyl-8α-ergolinyl]urea is dissolved under argon in 46 ml of chloroform. Then 3.5 g of silica gel and, under vigorous agitation, dropwise 3.5 ml of water are added. During a time period of 30 minutes, a solution of 1.18 ml of sulfuryl chloride in 30 ml of chloroform is added drop by drop. After stirring for 3 hours at room temperature, 7.5 g of potassium carbonate is added and the mixture is vigorously stirred for 20 minutes. The precipitate is filtered off and washed with chloroform. The precipitate is moistened with ethanol and introduced into 300 ml of saturated sodium chloride solution which is then repeatedly extracted with chloroform. The chloroform extracts and the chloroform filtrate are jointly dried over magnesium sulfate and evaporated. The subsequent crystallization is performed from ethyl acetate, thus isolating 0.93 g of 1,1-diethyl-3-(6-methyl-2-formyl-8α-ergolinyl)urea (54% yield).

$[\alpha]_D= +78°$ (0.5% in pyridine).

EXAMPLE 28

Under argon, 320 mg (8 mmol) of lithium aluminum hydride is suspended in 20 ml of absolute, freshly distilled tetrahydrofuran. At room temperature, a solution of 1.40 g (4 mmol) of 1,1-diethyl-3-(6-methyl-2-formyl-8α-ergolinyl)urea in 40 ml of freshly distilled, absolute tetrahydrofuran is added dropwise. Then the mixture is stirred for 1¼ hours at room temperature. The batch is then cooled in an ice bath and combined with 20 ml of 1N hydrochloric acid. To this mixture is added 20 ml of 2N tartaric acid and the batch is layered over the ethyl acetate. For neutralization, 80 ml of 1N ammonia solution is added dropwise. The ethyl acetate phase is separated, and the aqueous phase is reextracted with ethyl acetate. The combined ethyl acetate phases are dried over sodium sulfate. The concentrated crude product is chromatographed on silica gel with methylene chloride/methanol 95:5 under pressure. The crude product (1.09 g) is crystallized from ethyl acetate, thus obtaining 0.94 g of 1,1-diethyl-3-(6-methyl-2-hydroxymethyl-8α-ergolinyl)urea (65% yield).

$[\alpha]_D = +38°$ (0.5% in pyridine).

EXAMPLE 29

Under argon, 11.5 g (0.03 mol) of 3-(9,10-didehydro-6-methyl-8α-ergolinyl)-1,1-diethylurea is dissolved in 300 ml of chloroform. At room temperature, 105 ml of ethyl formate and 5.4 ml of ethanedithiol are added in succession. Then 13.2 ml of titanium(IV) chloride in 150 ml of chloroform is added dropwise. The mixture is agitated for 3 days at room temperature. To work up the mixture, it is cooled in an ice bath and 75 ml of methanol and 600 ml of water are added in sequence dropwise to this mixture. The solution is rendered alkaline with 60 ml of 25% ammonia solution and extracted with methylene chloride. The organic phases are washed with water and dried over magnesium sulfate. The concentrated residue is chromatographed under pressure on silica gel with ethyl acetate/methanol 95:5, thus isolating 1.7 g of 3-[9,10-didehydro-2-(1,3-dithiolan-2-yl)-6-methyl-8α-ergolinyl]-1,1-diethylurea (12% yield).

EXAMPLE 30

Under argon, 1.10 g (2.5 mmol) of 3-[9,10-didehydro-2-(1,3-dithiolan-2-yl)-6-methyl-8α-ergolinyl]-1,1-diethylurea is dissolved in 25 ml of chloroform and combined with 1.9 g of silica gel of a particle size of 0.063-0.2 mm. Under vigorous agitation, 2 ml of distilled water is added dropwise. Subsequently, within a time period of 15 minutes, a solution of 0.5 ml (0.6 mmol) of sulfuryl chloride in 13 ml of chloroform is added dropwise and the mixture is stirred for 2 hours at room temperature. For working-up purposes, 3 g of potassium carbonate is added and the mixture is vigorously agitated for 20 minutes. The precipitate is filtered off and washed with methylene chloride. The precipitate is moistened with ethanol and made into a slurry with 250 ml of saturated sodium chloride solution. This mixture is repeatedly extracted with methylene chloride. The extracts are dried together with the methylene chloride filtrate over magnesium sulfate and concentrated. The crude product is chromatographed under pressure on silica gel with a chloroform/methanol mixture and the main fraction of 448 mg is recrystallized from diisopropyl ether, thus obtaining 225 mg of 3-(9,10-didehydro-2-formyl-6-methyl-8α-ergolinyl)-1,1-diethylurea (25% yield).

$[\alpha]_D = +398°$ (0.5% in CHCl$_3$).

EXAMPLE 31

Under argon, a solution of 244 mg (0.67 mmol) of 3-(9,10-didehydro-2-formyl-6-methyl-8α-ergolinyl)-1,1-diethylurea in 25 ml of absolute, freshly distilled tetrahydrofuran is added dropwise to a suspension of 52 mg (1.45 mmol) of lithium aluminum hydride in 3 ml of absolute, freshly distilled tetrahydrofuran at room temperature. The mixture is stirred for one hour at room temperature. The batch is cooled in an ice bath and combined in succession with 3 ml of 1N hydrochloric acid and 3 ml of 2N tartaric acid. The mixture is layered over with ethyl acetate and made alkaline with 12 ml of 1N ammonia solution. The ethyl acetate phase is separated and the aqueous phase is additionally extracted twice with ethyl acetate. The combined ethyl acetate phases are dried over sodium sulfate and concentrated. The product is crystallized from ethyl acetate, yielding 161 mg of 3-(9,10-didehydro-2-hydroxymethyl-6-methyl-8α-ergolinyl)-1,1-diethylurea (65% yield).

$[\alpha]_D = +328°$ (0.5% in pyridine).

EXAMPLE 32

Analogously to Example 6, the corresponding lithium compound is obtained from 3-(2-bromo-1.tert-butoxydimethylsilyl-6-methyl-8α-ergolinyl)-1,1-diethylthiourea with tert-butyllithium, and from this compound, with dimethyl disulfide, the 1,1-diethyl-3-(6-methyl-2-methylthio-8α-ergolinyl)thiourea is obtained.

Yield: 38%; $[\alpha]_D = +54°$ (0.5% in chloroform).

EXAMPLE 33

Under argon, 0.3 ml (1.5 mmol) of distilled hexamethyldisilazane is added to 4 ml of absolute, freshly distilled toluene, and the mixture is cooled to 0° C. Then 0.85 ml (1.4 mmol) of 15% butyllithium/hexane is added dropwise and the mixture is stirred for 15 minutes at 0° C. To this mixture is added 531 mg (1 mmol) of 3-[2-bromo-1-(tert-butyldimethylsilyl)-9,10-didehydro-6-methyl-8α-ergolinyl]-1,1-diethylurea in 50 ml of absolute, freshly distilled toluene and agitation is continued for another 15 minutes at 0° C. After adding 1 ml of distilled tetramethylethylenediamine, the batch is cooled to −90° C. At this temperature, 5 ml (7 mmol) of 1.4M tert-butyllithium is added and the mixture is agitated for 2 minutes before 0.6 ml (5.4 mmol) of the methyl ester of trifluoromethanesulfonic acid is added thereto. After 1½ hours of agitation at −70° C., water is added to work up the reaction mixture. Extraction is performed with ethyl acetate. The organic phases are washed with saturated sodium bicarbonate solution and water. The combined ethyl acetate phases are dried over sodium sulfate and concentrated. Crystallization from methanol produces 128 mg of 3-[1-(tert-butyldimethylsilyl)-9,10-didehydro-2,6-dimethyl-8α-ergolinyl]-1,1-diethylurea (27% yield).

$[\alpha]_D = +252.1°$ (0.5% in CHCl$_3$).

EXAMPLE 34

Under argon, 183 mg (0.39 mmol) of 3-[1-(tertbutyldimethylsilyl)-9,10-didehydro-2,6-dimethyl-8α-ergolinyl]-1,1-diethylurea is dissolved in 5 ml of methanol with addition of 2 ml of tetrahydrofuran and stirred with 1 ml of 14N potassium hydroxide solution at room temperature for 17 hours. To work up the mixture, it is diluted with saturated sodium chloride solution and extracted with methylene chloride. The methylene chloride extracts are washed with saturated sodium chloride solution and water and dried over sodium sulfate. The crude product of 128 mg is chromatographed and crystallized as the tartrate, thus obtaining 94 mg (67% of theory) of 3-(9,10-didehydro-2,6-dimethyl-8α-ergolinyl)-1,1-diethylurea.

$[\alpha]_D = +222°$ (0.1% in pyridine).

Analogously, by replacing the trifluorosulfonic acid methyl ester by the ethyl ester, 3-(9,10-didehydro-2-ethyl-6-methyl-8α-ergolinyl)-1,1-diethylurea is obtained and crystallized as the tartrate. Yield: 21%;

$[\alpha]_D = +195°$ (0.1% in pyridine).

The following compounds are obtained by replacing the trifluoromethanesulfonic acid ester by the p-toluenesulfonic acid thio ester (ethyl, n-propyl and isopropyl):

3-(9,10-didehydro-2-ethylthio-6-methyl-8α-ergolinyl)-1,1-diethylurea. Yield: 26%; $[\alpha]_D = +299°$ (0.5% in chloroform);

3-(9,10-didehydro-6-methyl-2-n-propyl-8α-ergolinyl)-1,1-diethylurea. Yield: 38%; $[\alpha]_D = 284°$ (0.5% in chloroform);

3-(9,10-didehydro-6-methyl-2-isopropyl-8α-ergolinyl)-1,1-diethylurea. Yield: 21%; $[\alpha]_D = +286°$ (0.5% in chloroform).

Using as the starting material 3-[2-bromo-1-(tert-butyldimethylsilyl)-6-methyl-8α-ergolinyl]-1,1-diethylurea, then, with the ethyl ester of trifluoromethanesulfonic acid, 3-(2-ethyl-6-methyl-8α-ergolinyl)-1,1-diethylurea is obtained. Yield: 29%;

with the thioethyl ester of p-toluenesulfonic acid, 3-(2-ethylthio-6-methyl-8α-ergolinyl)-1,1-diethylurea. Yield: 78%; $[\alpha]_D = +5°$ (0.5% in chloroform);

with the thio-n-propyl ester of p-toluenesulfonic acid, 1,1-diethyl-3-(6-methyl-2-n-propylthio-8α-ergolinyl)urea. Yield: 75%; $[\alpha]_D = +4°$ (0.5% in chloroform);

with the thio-isopropyl ester of p-toluenesulfonic acid, 1,1-diethyl-3-(6-methyl-2-isopropylthio-8α-ergolinyl)urea. Yield: 35%; $[\alpha]_D = +4°$ (0.5% in chloroform); and with the phenylcyanate, 3-(2-cyano-6-methyl-8α-ergolinyl)-1,1-diethylurea. Yield: 12%; $[\alpha]_D = 0.5\%$ in pyridine).

EXAMPLE 35

1.4 g (3 mmol) of 3-(2-iodo-6-methyl-8α-ergolinyl)-1,1-diethylurea, 37.5 mg (0.123 mmol) of tri-o-tolylphosphine, 25.1 mg (0.032 mmol) of trans-dichloro-bis(tri-o-tolylphosphine) palladium (II) and 1.13 ml (7.8 mmol) of vinyltrimethylsilane are dissolved in 7.5 ml of trimethylformamide and 7.5 ml of triethylamine and, after purging with argon, heated in an autoclave for 3 hours to 100° C. After concentration of the reaction solution under reduced pressure, the solution is taken up in dichloromethane and washed with saturated sodium chloride solution. After drying over magnesium sulfate, the organic phase is concentrated. The crude product yields, after column chromatography over silica gel with dichloromethane/ethanol 10:1 as the eluent and recrystallization from ethanol/petroleum ether, 400 mg of 3-[6-methyl-2-(trans-2-trimethylsilyl-1-ethenyl)-8α-ergolinyl]-1,1-diethylurea (30.2%), mp 194°–197° C.; $[\alpha]_D = +89.0°$ (c=0.225% in pyridine); and 563 mg of 3-(2-ethenyl-6-methyl-8α-ergolinyl)-1,1-diethylurea (51.2%), mp 145°–150° C.; $[\alpha]_D = +63.5°$ (c=0.23% in pyridine).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ergoline substituted in the 2-position of the formula

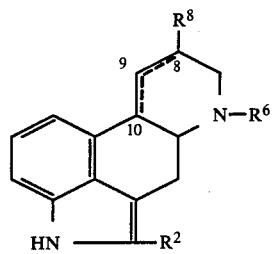

wherein
$C_8 \text{---} C_9$ and $C_9 \text{---} C_{10}$ each independently is a CC-single or a C=C-bond, but not a cumulated double bond, and the substituent in the 8-position is in the α- or β-configuration where $C_8 \text{---} C_9$ is a CC-single bond, $R^2$ is

SOR,

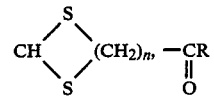

or —CH(OH)R wherein R is H or $C_{1-4}$-alkyl and n is 2 or 3;

COR' OR CSR' wherein R'=OH, $OC_{1-4}$-alkyl, benzyl, $NH_2$ or NHR'';

CH=CH—$CO_2R''$ or $CH_2$—$CH_2$—$CO_2R''$ wherein $R''=C_{1-4}$ alkyl,

C≡C—R''' or HC=CH—R''' wherein R'''=hydrogen, C1-4-alkyl, phenyl, $CH_2OH$, $CR''_2OH$

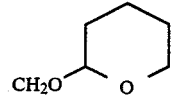

$CO_2R$, $CH_2NR''_2$ or $SiMe_2R''$; $C_{1-3}$-alkyl substituted by OH or phenyl; or

wherein R'' is $C_{1-4}$-alkyl,
$R^6$ is $C_{1-4}$-alkyl and
$R^8$ is methyl, NH—CO—$NEt_2$ or NH—CS—$NEt_2$, or a physiologically acceptable acid addition salt thereof.

2. A compound of claim 1 wherein $R^8$ is NH—CO—$NEt_2$.

3. A compound of claim 2 wherein $C_8 \text{---} C_9$ is a C=C-double bond and $C_9 \text{---} C_{10}$ is a CC single bond.

4. A compound of claim 2 wherein $C_8\text{---}C_9$ is a CC single bond and $C_9\text{---}C_{10}$ is a C=C double bond.

5. A compound of claim 1 wherein $R^8$ is NH—C-S—NEt$_2$.

6. A compound of claim 5 wherein $C_8\text{---}C_9$ is a C=C-double bond and $C_9\text{---}C_{10}$ is a CC single bond.

7. A compound of claim 5 wherein $C_8\text{---}C_9$ is a CC single bond and $C_9\text{---}C_{10}$ is a C=C double bond.

8. A compound of claim 1 wherein $R^8$ is methyl.

9. A compound of claim 8 wherein $C_8\text{---}C_9$ is a C=C double bond and $C_9\text{---}C_{10}$ is a CC single bond.

10. A compound of claim 8 wherein $C_8\text{---}C_9$ is a CC single bond and $C_9\text{---}C_{10}$ is a C=C double bond.

11. 1,1-Diethyl-(6-methyl-2-ethynyl-8α-ergolinyl)urea, a compound of claim 1.

12. A pharmaceutical composition for treating depression comprising an effective amount of a 2-substituted ergolinyl compound of claim 1 and a pharmaceutically acceptable carrier.

13. A method of achieving neuroleptic effect in a patient comprising administering an effective amount of an ergolinyl compound of claim 1.

14. A method of treating depression in a patient comprising administering to the patient an antidepressantly effective amount of an ergolinyl compound of claim 1.

* * * * *